US008483470B2

(12) United States Patent
Ohno

(10) Patent No.: US 8,483,470 B2
(45) Date of Patent: Jul. 9, 2013

(54) RADIOLOGICAL IMAGE AREA EXTRACTING APPARATUS, RADIOLOGICAL IMAGE AREA EXTRACTION PROGRAM, AND RADIOGRAPHIC APPARATUS

(75) Inventor: Yoshinori Ohno, Kyotanabe (JP)

(73) Assignee: Shimadzu Corporation, Kyoto (JP)

( * ) Notice: Subject to any disclaimer, the term of this patent is extended or adjusted under 35 U.S.C. 154(b) by 276 days.

(21) Appl. No.: 13/079,863

(22) Filed: Apr. 5, 2011

(65) Prior Publication Data

US 2011/0305381 A1    Dec. 15, 2011

(30) Foreign Application Priority Data

Jun. 10, 2010 (JP) ................................. 2010-133066

(51) Int. Cl.
*G06K 9/00* (2006.01)
*B41M 5/00* (2006.01)

(52) U.S. Cl.
USPC .............................. 382/132; 382/274; 378/28

(58) Field of Classification Search
USPC ................. 382/100, 103, 107, 128–133, 168, 382/172, 173, 181, 190, 194, 199, 232, 240, 382/254, 263, 276, 305, 312; 378/4, 16, 28
See application file for complete search history.

(56) References Cited

U.S. PATENT DOCUMENTS

| 5,960,102 A | * | 9/1999 | Van Eeuwijk et al. | ........ 382/128 |
| 6,611,627 B1 | * | 8/2003 | LaRossa et al. | ............. 382/240 |
| 6,956,972 B2 | | 10/2005 | Young | |
| 6,956,975 B2 | * | 10/2005 | Young | ............................ 382/263 |
| 8,160,346 B2 | * | 4/2012 | Gatesoupe et al. | ........... 382/132 |

FOREIGN PATENT DOCUMENTS

| JP | 2002-369079 A | * | 12/2002 |
| JP | 4143149 B2 | | 9/2008 |

* cited by examiner

*Primary Examiner* — Seyed Azarian
(74) *Attorney, Agent, or Firm* — Cheng Law Group, PLLC

(57) ABSTRACT

An image area extracting device includes a low-frequency image generating unit for generating a low-frequency image from a radiological image by a frequency filter process lower than a spatial frequency inside an object area, a luminance variation image generating unit for generating a luminance variation image by detecting luminance variations of the low-frequency image, and a boundary selecting unit for selecting boundary pixels located on a boundary of an area of interest based on pixel values of the luminance variation image and the low-frequency image. Influences of noise components or fine structural components inside a patient M are reduced by generating the low-frequency image, which facilitates recognition of a contour shape of the patient M. The boundary pixels are selected based on the low-frequency image and the luminance variation image generated from the low-frequency image. This assures highly accurate and stable area extraction.

19 Claims, 8 Drawing Sheets

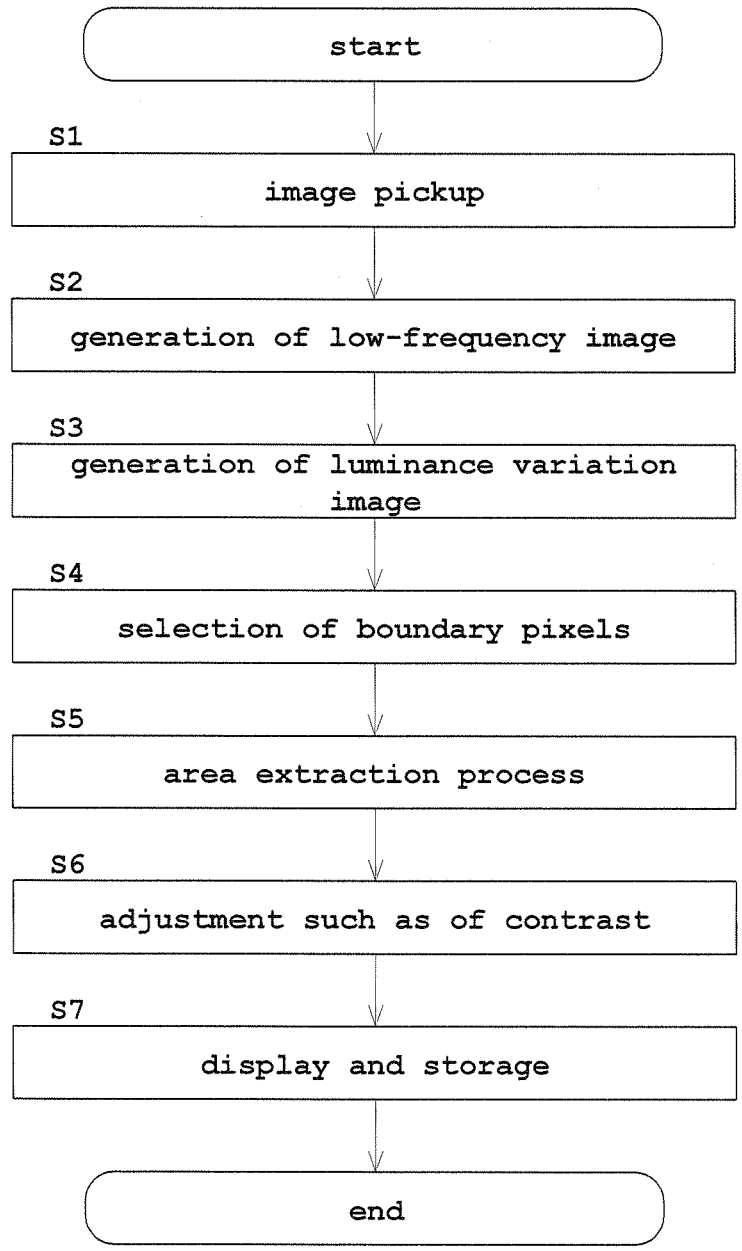

Fig.9A
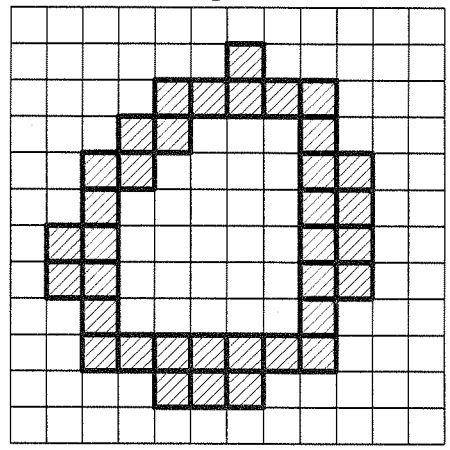
Fig.9B
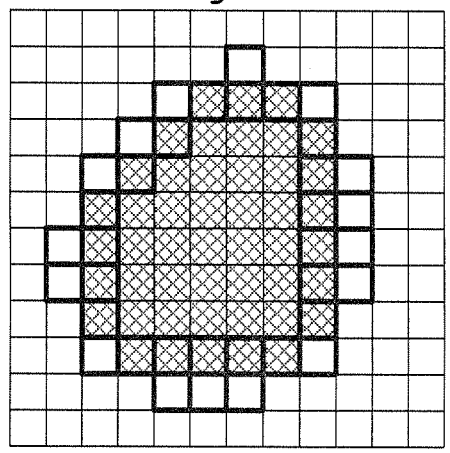
Fig.9C
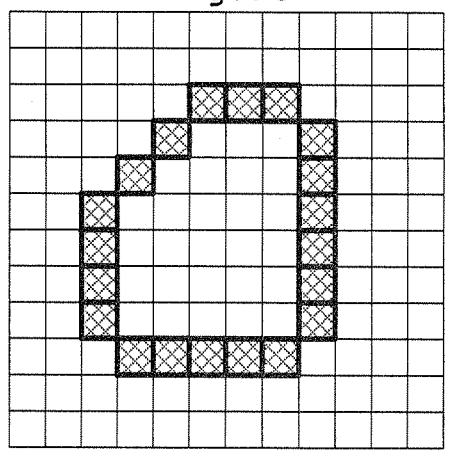

RADIOLOGICAL IMAGE AREA EXTRACTING APPARATUS, RADIOLOGICAL IMAGE AREA EXTRACTION PROGRAM, AND RADIOGRAPHIC APPARATUS

BACKGROUND OF THE INVENTION (1) Field of the Invention

This invention relates to a radiological image area extracting apparatus, a radiological image area extraction program and a radiographic apparatus for selecting an area of interest of an object under examination from radiological images picked up.

(2) Description of the Related Art

In order to secure images suitable for diagnosis, a radiographic apparatus extracts an area of interest of a patient from radiological images obtained by detecting radiation (e.g. X-rays or gamma rays), and carries out various image processes on the extracted area of interest of the patient. In radiographing the chest of the patient, what is needed particularly for diagnosis is a lung field area in the radiological images. In the radiological images, however, the abdomen and arms unnecessary for diagnosis and areas directly irradiated with radiation will also be included along with the lung field area required for diagnosis. These areas are greatly different in image density and contrast from the area of interest which is the lung field area of the patient. In order to carry out image processes with increased efficiency, it is required to exclude the areas other than the area of interest from areas subjected to the image processes (see Japanese patent No. 4143149, for example).

According to Japanese patent No. 4143149, in order to extract the lung field area of a patient first, a process is carried out to binarize an image based on a threshold, and a labeling process is carried out for the binarized image. Then, among a plurality of areas subjected to the labeling process, areas below a predetermined size are removed as areas showing high density outside the lung field area, and areas adjacent the top, bottom, left and right ends of the image are removed as areas directly irradiated with X-rays. On the other hand, areas not removed are selected as lung field area. A threshold is estimated from a maximum pixel value and a minimum pixel value, in which, for example, the maximum pixel (density) value is calculated from the image area of the patient from which the directly irradiated areas are removed, and the minimum pixel value is calculated from recesses of a profile passing through the coordinates of this maximum pixel value.

Another apparatus of this type is disclosed in Japanese Unexamined Patent Publication No. 2002-369079, for example. According to this publication, in order to remove a background space (directly irradiated area) providing no diagnostic information from a mammographic image first, a binary image is produced based on a threshold. Then, skin line pixels are determined to select an area.

Such a conventional apparatus sets a threshold for removing the directly irradiated area, and an area value for excluding areas below a predetermined area which have been extracted in error, or a threshold for selecting an area of interest of a patient. However, the conventional apparatus has a drawback that, when subjects of radiography or radiographing conditions are changed, for example, area extraction cannot be carried out with high accuracy unless optimal values are set all over again each time such a change takes place.

There is a further drawback that, under the influence of the threshold, noise and so on, the area selected can be altered and variations can occur in accuracy. Further, areas are detected by the binarization process and labeling process of an entire image, and these processes are time-consuming and susceptible to the influence of noise, for example.

SUMMARY OF THE INVENTION

This invention has been made having regard to the state of the art noted above, and its object is to provide a radiological image area extracting apparatus, a radiological image area extraction program and a radiographic apparatus which enable a highly accurate and stable area extraction.

The above object is fulfilled, according to this invention, by a radiological image area extracting apparatus for extracting an area of interest of an object under examination from a radiological image picked up, the apparatus comprising a low-frequency image generating unit for generating a low-frequency image from the radiological image by a frequency filter process lower than a spatial frequency inside an object area; a luminance variation image generating unit for generating a luminance variation image by detecting luminance variations of the low-frequency image; and a boundary selecting unit for selecting boundary pixels located on a boundary of the area of interest based on pixel values of the luminance variation image and the low-frequency image.

According to the radiological image area extracting apparatus of this invention, the low-frequency image generating unit generates a low-frequency image from a radiological image by a frequency filter process lower than the spatial frequency in the area of the object. The luminance variation image generating unit detects luminance variations of the low-frequency image, and generates a luminance variation image. That is, influences of noise components or fine structural components inside the object are reduced by generating the low-frequency image, which facilitates recognition of a contour shape of the object. The luminance variation image generated from the low-frequency image provides the same effect as the low-frequency image. The boundary selecting unit selects boundary pixels located on the boundary of the area of interest of the object based on such luminance variation image and low-frequency image. This assures highly accurate and stable area extraction.

In the above radiological image area extracting apparatus, it is preferred that the low-frequency image generating unit is arranged to generate the low-frequency image by reducing the radiological image. This can generate a low-frequency image of lower frequency than with a usual filter, which realizes a reduced influence of disturbance such as of noise, thereby assuring highly accurate and stable area extraction. Since the low-frequency image is used to generate the luminance variation image and select boundary pixels, data amounts used in calculations can be made relatively small and the area of interest of the object can be extracted at high speed.

In the above radiological image area extracting apparatus, it is preferred that the radiological image is reduced, when a reduction ratio is 1/n, by making an average pixel value of n×n pixels a pixel value of one pixel. In one example of radiological image reduction, when a reduction ratio is 1/n, an average pixel value of pixels thinned out of n×n pixels is made a pixel value of one pixel. The low-frequency image can be generated by reducing the radiological image in such ways. When the pixels are thinned out, data amounts can be lessened for calculations performed at the time of reduction.

The radiological image area extracting apparatus, preferably, further comprises an area extraction processing unit for carrying out a process for enlarging the boundary pixels selected by the boundary selecting unit to a size of the radiological image, and a process for extracting the area of interest from the radiological image. When the low-frequency image is generated by reducing the radiological image, the area of interest of the object can be extracted from the radiological image by carrying out the process for enlargement back to the size of the radiological image.

In the above radiological image area extracting apparatus, one example of the boundary selecting unit is arranged to select the boundary pixels of the area of interest by selecting an initial pixel which is a pixel of maximum luminance variation from the luminance variation image, selecting as a next boundary pixel a pixel of maximum luminance variation from among pixels adjoining the selected initial pixel in all directions, and thereafter repeatedly selecting as a next boundary pixel a pixel of maximum luminance variation from among adjacent pixels located in a direction of movement of a selected pixel. Each boundary pixel is a pixel of maximum luminance variation selected from among pixels adjacent a preceding selected pixel in the luminance variation image generated from the low-frequency image. This assures highly accurate and stable area extraction.

In the above radiological image area extracting apparatus, it is preferred that the boundary selecting unit is arranged, when a pixel value of a pixel newly selected in the luminance variation image is below a predetermined value, to select as a next boundary pixel a pixel with a value closest to a pixel value of a pixel in the low-frequency image corresponding in position to a pixel before selection in the luminance variation image, from among pixels adjacent the pixel in the low-frequency image. When the pixel value of the pixel newly selected in the luminance variation image by the boundary selecting unit is below the predetermined value, the newly selected pixel is determined low in reliability as boundary pixel. That is, the smaller the luminance variation is, the lower is reliability as boundary pixel. In this case, a pixel in the low-frequency image with a value closest to the pixel value of a pixel before selection is selected as a next boundary pixel from among pixels adjacent the pixel before selection. Selecting the pixel with the closest pixel value indicates a high possibility of the pixel being in the same area and being a boundary pixel. Thus, the newly selected pixels determined low in reliability are ruled out. Even when pixels are determined low in reliability, boundary pixels are selected from the low-frequency image, thereby assuring highly accurate and stable area extraction.

In the above radiological image area extracting apparatus, it is preferred that the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image. When the result of comparison between pixel values of pixels in the low-frequency image corresponding in position to a newly selected pixel and a pixel before selection in the luminance variation image is larger than the predetermined value, the newly selected pixel is determined low in reliability as boundary pixel. That is, even in the case of a pixel with a large luminance variation (i.e. even if the pixel value of the newly selected pixel and the pixel value of the pixel before selection are similar), pixel values can be widely different in the low-frequency image. In this case also, a pixel in the low-frequency image with a value closest to the pixel value of a pixel before selection is selected as a next boundary pixel from among pixels adjacent the pixel before selection. Selecting the pixel with the closest pixel value indicates a high possibility of the pixel being in the same area and being a boundary pixel. Thus, the newly selected pixels determined low in reliability are ruled out. Even when pixels are determined low in reliability, boundary pixels are selected from the low-frequency image, thereby assuring highly accurate and stable area extraction.

In another aspect of the invention, a radiological image area extraction program is provided for causing a computer to carry out a process for extracting an area of interest of an object under examination from a radiological image picked up, the program comprising a step of generating a low-frequency image from the radiological image by a frequency filter process lower than a spatial frequency inside an object area; a step of generating a luminance variation image by detects luminance variations of the low-frequency image; and a step of selecting boundary pixels located on a boundary of the area of interest based on pixel values of the luminance variation image and the low-frequency image.

According to the radiological image area extraction program of this invention, a low-frequency image is generated from a picked up radiological image by a frequency filter process lower than the spatial frequency in the area of the object. Luminance variations of this low-frequency image are detected to generate a luminance variation image. Based on pixel values of the luminance variation image and low-frequency image generated, boundary pixels located on the boundary of the area of interest of the object are detected, with image density and contrast greatly varying at the boundary. Influences of noise components or fine structural components inside the object are reduced by generating the low-frequency image from the radiological image, which facilitates recognition of a contour shape of the object. By generating the luminance variation image from the low-frequency image, the luminance variation image provides the same effect as the low-frequency image. Boundary pixels located on the boundary of the area of interest of the object are selected based on such luminance variation image and low-frequency image. This assures highly accurate and stable area extraction.

In a further aspect of the invention, a radiographic apparatus is provided for picking up images of an object under examination, the apparatus comprising a radiation detector for detecting radiation; and an image area extracting device for extracting an area of interest of the object from a radiological image outputted from the radiation detector; wherein the image area extracting device includes a low-frequency image generating unit for generating a low-frequency image from the radiological image by a frequency filter process lower than a spatial frequency inside an object area, a luminance variation image generating unit for generating a luminance variation image by detecting luminance variations of the low-frequency image, and a boundary selecting unit for selecting boundary pixels located on a boundary of the area of interest based on pixel values of the luminance variation image and the low-frequency image.

According to the radiographic apparatus of this invention, the radiation detector detects radiation and outputs radiological images. The image area extracting device extracts an area of interest of the object from a radiological image outputted from the radiation detector. In the image area extracting device, the low-frequency image generating unit generates a low-frequency image from the radiological image by a frequency filter process lower than the spatial frequency in the area of the object to reduce the spatial resolution of the radiological image. The luminance variation image generating unit detects luminance variations of the low-frequency image, and generates a luminance variation image. Boundary pixels located on the boundary of the area of interest of the object where image density and contrast are greatly different are selected based on pixel values of the luminance variation image and low-frequency image generated. Influences of noise components or fine structural components inside the object are reduced by generating the low-frequency image from the radiological image, which facilitates recognition of a contour shape of the object. The luminance variation image generated from the low-frequency image provides the same effect as the low-frequency image. The boundary selecting unit selects boundary pixels located on the boundary of the area of interest of the object based on such luminance variation image and low-frequency image. This assures highly accurate and stable area extraction.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 7 is a flow chart showing operation of the radiographic apparatus;

FIG. 9A is a view showing operation, with respect to a luminance variation image, of a boundary selecting unit according to a modification;

FIG. 9B is a view showing operation, with respect to a low-frequency image, of the boundary selecting unit according to the modification;

FIG. 9C is a view showing selected boundary pixels in operation of the boundary selecting unit according to the modification;

DESCRIPTION OF THE PREFERRED EMBODIMENTS

Preferred embodiments of this invention will be described in detail hereinafter with reference to the drawings.

Embodiment

Figure 1:
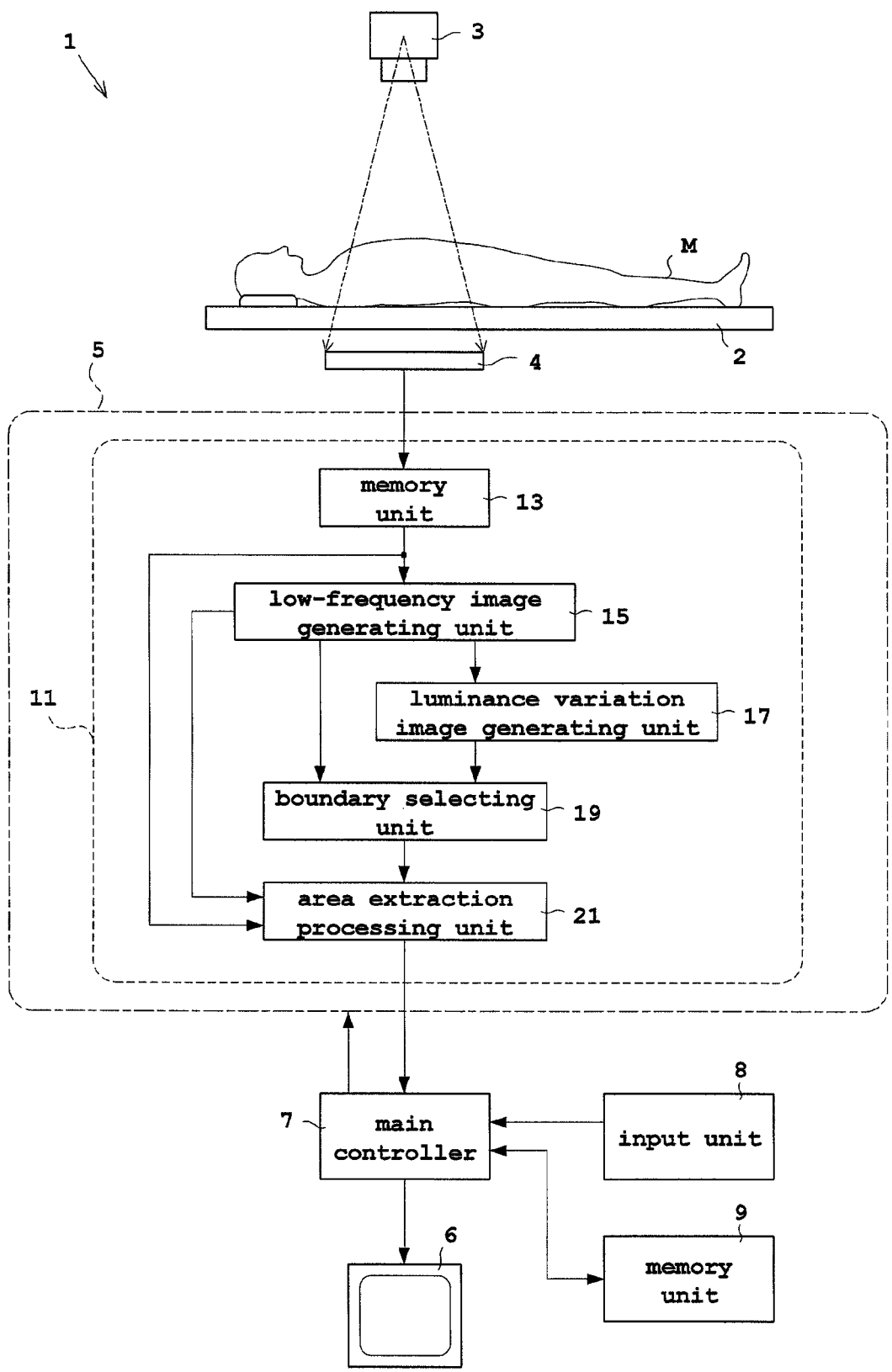
FIG. 1 is a view showing an outline construction of a radiographic apparatus according to this invention.
Figure 2:
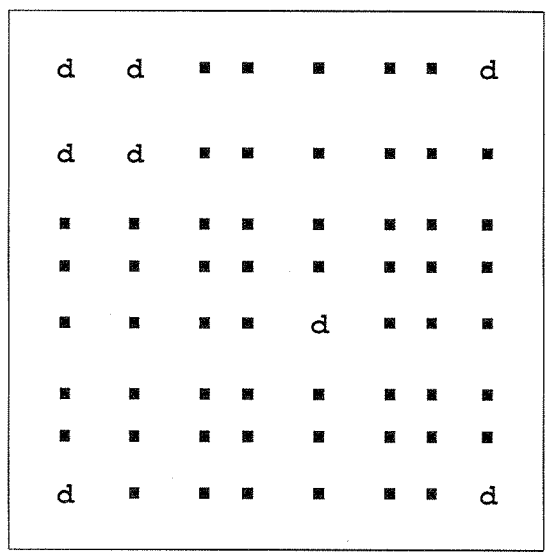
FIG. 2 is a schematic view of a detecting plane of a flat panel radiation detector (FPD)
Figure 3A:
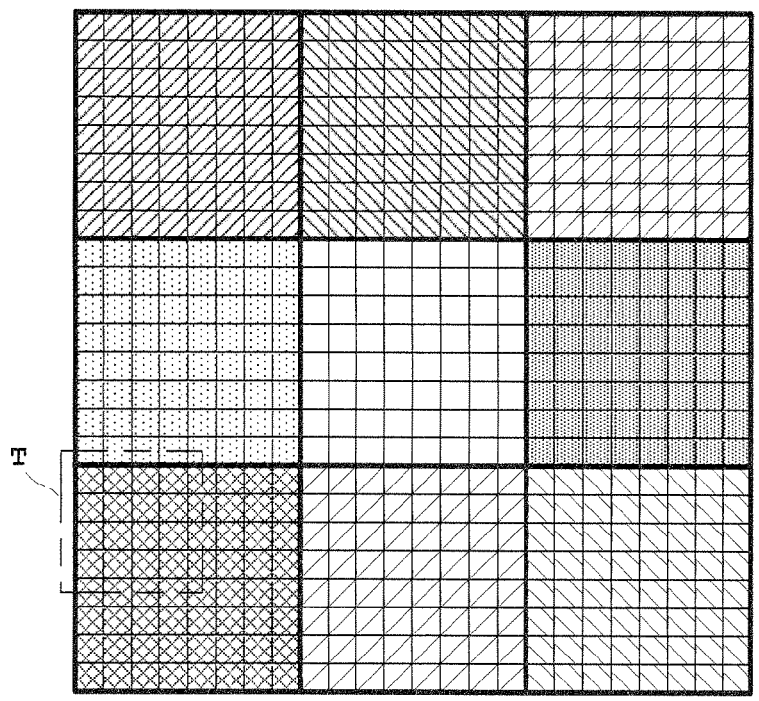
FIG. 3A is a view showing pixels before reduction in operation of a low-frequency image generating unit.
Figure 3B:
FIG. 3B is a view showing pixels after reduction in operation of the low-frequency image generating unit.
Figure 4:
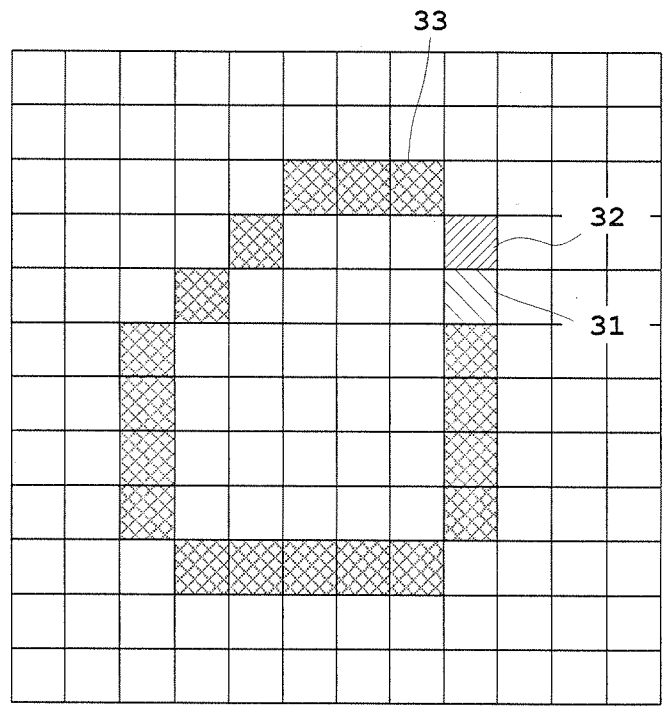
FIG. 4 is an explanatory view depicting operation of a boundary selecting unit.
Figure 5A:
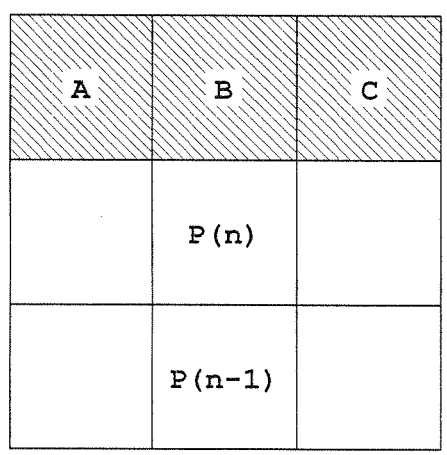
FIG. 5A is a view showing three pixels searched when a direction of movement is vertical or horizontal, in operation of the boundary selecting unit.
Figure 5B:
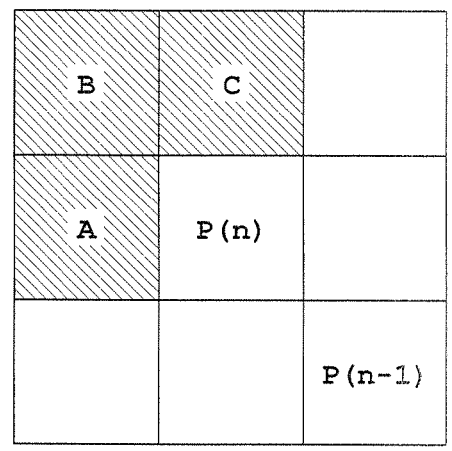
FIG. 5B is a view showing three pixels searched when a direction of movement is oblique, in operation of the boundary selecting unit.
Figure 6A:
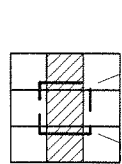
FIG. 6A is a view showing boundary pixels before enlargement in operation of an area extraction processing unit.
Figure 6B:
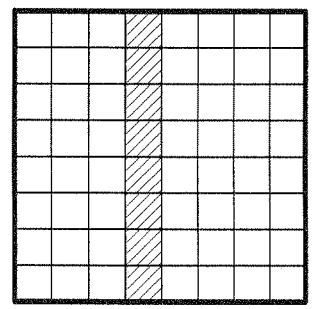
FIG. 6B is a view showing boundary pixels after enlargement in operation of the area extraction processing unit.

An embodiment of this invention will be described hereinafter with reference to the drawings. FIG. 1 is a view showing an outline construction of a radiographic apparatus according to this invention. FIG. 2 is a schematic view of a detecting plane of a flat panel radiation detector (FPD). FIG. 3A is a view showing pixels before reduction in operation of a low-frequency image generating unit. FIG. 3B is a view showing pixels after reduction in operation of the low-frequency image generating unit. FIG. 4 is an explanatory view depicting operation of a boundary selecting unit. FIG. 5A is a view showing three pixels searched when a direction of movement is vertical or horizontal, in operation of the boundary selecting unit. FIG. 5B is a view showing three pixels searched when a direction of movement is oblique, in operation of the boundary selecting unit. FIG. 6A is a view showing boundary pixels before enlargement in operation of an area extraction processing unit. FIG. 6B is a view showing boundary pixels after enlargement in operation of the area extraction processing unit.

<Radiographic Apparatus>

Reference is made to FIG. 1. A radiographic apparatus 1 according to this embodiment includes a top board 2 for supporting a patient M, a radiation source (e.g. an X-ray tube) 3 for emitting radiation (e.g. X-rays) toward the patient M, and a flat panel radiation detector (hereinafter abbreviated as "FPD") 4 opposed to the radiation source 3 for detecting radiation transmitted through the patient M.

The radiation source 3 is controlled by an emission controller not shown. When emitting X-rays, for example, the emission controller performs control of the radiation source 3 required for emission according to emitting conditions, such as tube voltage and/or tube current, set beforehand at an input unit 8 which will be described hereinafter.

As shown in FIG. 2, the FPD 4 has detecting elements d arranged in a two-dimensional matrix form on a detecting plane. The detecting elements d convert radiation transmitted through the patient M into electric signals corresponding to intensity levels of the radiation, and store the electric signals once. The radiation is detected by reading the electric signals stored. A radiological image is outputted by allotting an electric signal detected by each detecting element d as a pixel value of each pixel.

Returning to FIG. 1, an image processor 5 is disposed downstream of the FPD 4, and is connected thereto through an analog-to-digital converter not shown. The image processor 5 carries out various image processes for radiological images provided by the FPD 4. The radiological images resulting from the various image processes are displayed on a display unit 6 including a monitor.

The radiographic apparatus 1 includes a main controller 7, the input unit 8 and a memory unit 9. The main controller 7 is formed of a central processing unit (CPU), for example, for executing various programs to carry out controls to operate appropriately components such as the radiation source 3, FPD 4 and image processor 5. The input unit 8 is operable by the operator to input settings such as radiation emitting conditions. The memory unit 9 includes storage media such as a ROM (Read-only Memory), a RAM (Random-Access Memory) and/or a hard disk for storing radiological images acquired.

The image processor 5 is formed of a CPU, for example. Programs and the like for carrying out various image processes are written and stored in storage media such as a ROM and a RAM, and the CPU of image processor 5 reads the programs and the like from the storage media to carry out image processes corresponding to the programs. The image processor 5 includes an image area extracting unit 11 for extracting an area of interest of the patient M from radiological images obtained. The image area extracting unit 11 corresponds to the radiological image area extracting apparatus in this invention.

<Image Area Extracting Unit>

The image area extracting unit 11 includes a memory unit 13, a low-frequency image generating unit 15, a luminance variation image generating unit 17, a boundary selecting unit 19 and an area extraction processing unit 21. The memory unit 13 stores radiological images acquired by the FPD 4.

The low-frequency image generating unit 15 uses a radiological image stored in the memory unit 13 as an input image, and carries out a frequency filter process lower than a spatial frequency inside the patient M to generate a low-frequency image with reduced spatial resolution (blurred) from the radiological image. As shown in FIGS. 3A and 3B, for example, the low-frequency image generating unit 15 generates a low-frequency image by reducing the radiological image. As a specific example, when a lung field area is extracted from a chest frontal image, the size of the low-frequency image (reduced image), preferably, is about ⅛ to ¹/₁₀ of the original radiological image. When reducing the image to one eighth as shown in FIG. 3A, for example, an average pixel value of 8×8 pixels arranged vertically and horizontally in the radiological image is made one pixel as shown in FIG. 3B. Each location with the same hatched pattern in FIGS. 3A and 3B represents the pixels before and after the reduction.

The luminance variation image generating unit 17 detects luminance variations in the low-frequency image generated by the low-frequency image generating unit 15, and generates a luminance variation image. The luminance variation image generating unit 17 calculates luminance gradients as amounts of characteristic, for example. The calculations of the luminance gradients are expressed by the following equations (1) and (2):

$$Ex(x,y)=I(x+1,y)-I(x-1,y) \quad (1)$$

$$Ey(x,y)=I(x,y+1)-I(x,y-1) \quad (2)$$

where I(x, y) is a pixel value of a pixel with coordinates (x, y), Ex(x, y) is an amount of characteristic in the direction of x-axis, and Ey(x, y) is an amount of characteristic in the direction of y-axis.

Intensity of a luminance gradient P(x, y) is calculated from the following equation (3):

$$P(x,y)=\sqrt{[\{Ex(x,y)\}^2+\{Ey(x,y)\}^2]} \quad (3)$$

The boundary selecting unit 19 selects boundary pixels located on the boundary of the area of interest, based on the pixel value of each pixel in the luminance variation image and low-frequency image generated by the low-frequency image generating unit 15 and luminance variation image generating unit 17.

The boundary selecting unit 19 selects an initial pixel from the luminance variation image, which initial pixel is a pixel having the largest luminance variation, and selects a next pixel which is a pixel having the largest luminance variation from among pixels adjacent the selected initial pixel and located in all directions therefrom. Then, the boundary selecting unit 19 repeats selecting a pixel with the largest luminance variation from among pixels adjacent a selected pixel in a direction of movement of the selected pixel, thereby to select boundary pixels of the area.

The boundary selecting unit 19 first selects an initial pixel which is a pixel having the largest luminance variation from the luminance variation image. As shown in FIG. 4, for example, a pixel 31 having the largest luminance variation is selected from the luminance variation image. When radiation at the radiation source 3 and FPD 4 is restricted by a collimator not shown, the initial pixel 31 is selected from an irradiation field range of the luminance variation image. Next, a pixel having the largest luminance variation is selected as a next boundary pixel from among eight pixels adjacent the selected initial pixel 31 and located in all directions therefrom. As shown in FIG. 4, for example, the eight pixels around the initial pixel 31 are searched, and a pixel 32 having the largest luminance variation is selected as a next boundary pixel.

Subsequently, the boundary selecting unit 19 selects a pixel with the largest luminance variation as a next boundary pixel from among adjacent pixels located in a direction of movement of a selected pixel. Specifically, as shown in FIGS. 5A and 5B, the boundary selecting unit 19 searches three adjacent pixels located in the direction of movement which extends a boundary line formed of boundary pixels. As shown in FIG. 5A, for example, P(n) denotes an nth selected pixel which is a currently selected pixel, and P(n−1) denotes an immediately preceding, selected pixel. Since the boundary line extends from P(n−1) to P(n), this direction is the direction of movement. The three adjacent pixels located in the direction of movement of the selected pixel include pixel B opposed to pixel P(n−1) across pixel P(n), and pixel A and pixel C disposed at opposite sides of pixel B so as to surround pixel P(n). That is, the three pixels consisting of pixel A, pixel B and pixel C are searched. A pixel having the largest luminance variation among the three pixels is selected as a next pixel. This applies also to the example shown in FIG. 5B. As shown in FIG. 4, for example, where pixel P(n) is pixel 32 and pixel P(n−1) is pixel 31, the three adjacent pixels located in the direction of movement of pixel 32 are searched, and a pixel having the largest luminance variation among these pixels, e.g. pixel 33, is selected as a next boundary pixel.

The boundary selecting unit 19 determines whether the pixel selected (e.g. pixel 33) has already been selected. When this pixel has not been selected yet, the boundary selecting unit 19 repeats the process of selecting a next boundary pixel from three adjacent pixels located in the direction of movement of the selected pixel. On the other hand, when the pixel in question has already been selected, the boundary selecting unit 19 ends the selecting process, and outputs image data indicating selected boundary pixels as shown in FIG. 4, for example.

The boundary pixels outputted from the boundary selecting unit 19 are not limited to the image data of the boundary pixels shown in FIG. 4. That is, the boundary selecting unit 19 may output data as a binary image showing the inside and outside of the area of interest. The boundary selecting unit 19 may hold coordinate data of the selected boundary pixels, and may output this data as a coordinate data group.

The area extraction processing unit 21 carries out a process of enlarging the boundary pixels selected by the boundary selecting unit 19 to the size of the original radiological image which is the radiological image before being inputted to the low-frequency image generating unit 15, and a process of extracting the area of interest of the patient M from the original radiological image. The area extraction processing unit 21 receives the boundary pixels selected by the boundary selecting unit 19, the original radiological image transferred from the memory unit 13, and a signal of an image reduction ratio for generating the low-frequency image, which signal is transferred from the low-frequency image generating unit 15.

That is, the area extraction processing unit 21 carries out a process for extracting the area of interest of the patient M from the original radiological image based on the boundary pixels, original radiological image and image reduction ratio. First, a process for enlargement to the size of the original radiological image is carried out based on the boundary pixels and image reduction ratio. For example, the boundary pixel data is enlarged eight times when the low-frequency image is generated by a ⅛ image reduction ratio. Specifically, one of the boundary pixels shown in FIG. 6A is enlarged to 8×8 pixels in vertical and horizontal directions as shown in FIG. 6B. At this time, a column of pixels located at the middle of the 8×8 pixels and having an arbitrary width (e.g. corresponding to one pixel) is regarded as boundary pixels. Setting the narrow width to the boundary pixels can leave increased image information adjacent the boundary pixels.

The location of the boundary pixels is not limited to the middle of the enlarged image. Assume, for example, that the right portions of FIGS. 6A and 6B correspond to the inside of the area. When a leftward column of pixels representing the outside of the area, among the enlarged 8×8 pixels, is selected as boundary pixels, an area including the boundary and the outside of the boundary can be extracted, which enables confirmation of accuracy of the area extraction. When a rightward column of pixels representing the inside of the area, among the enlarged 8×8 pixels, is selected as boundary pixels, an area excluding unwanted parts, such as the boundary and the outside of the boundary, can be extracted. When a column of pixels at the right end is selected as boundary pixels, the same effect is provided as when all the 8×8 pixels are used as boundary pixels. The signal of the image reduction ratio is not limited to being transferred from the low-frequency image generating unit 15, but may be applied from the main controller 7, for example.

Next, the area extraction processing unit 21 carries out a process of extracting the area of interest of the patient M from the original radiological image based on the enlarged boundary pixel data. That is, the area extraction processing unit 21 extracts the area of interest of the patient M by dividing areas in positions of the enlarged boundary image from the original radiological image. The area extraction processing unit 21 displays lines indicating the area of interest on the radiological image, for example, or sets a pixel value to darken pixels outside the extracted area of interest (e.g. sets the pixel value to 0). The image processor 5 carries out other required image processes such as contrast control of the radiological image with the area of interest of the patient M extracted by the image area extracting unit 11. The radiological image having undergone the other required image processes by the image processor 5 is displayed on the display unit 6 and/or stored in the memory unit 9.

<Description of Operation>

Figure 8:
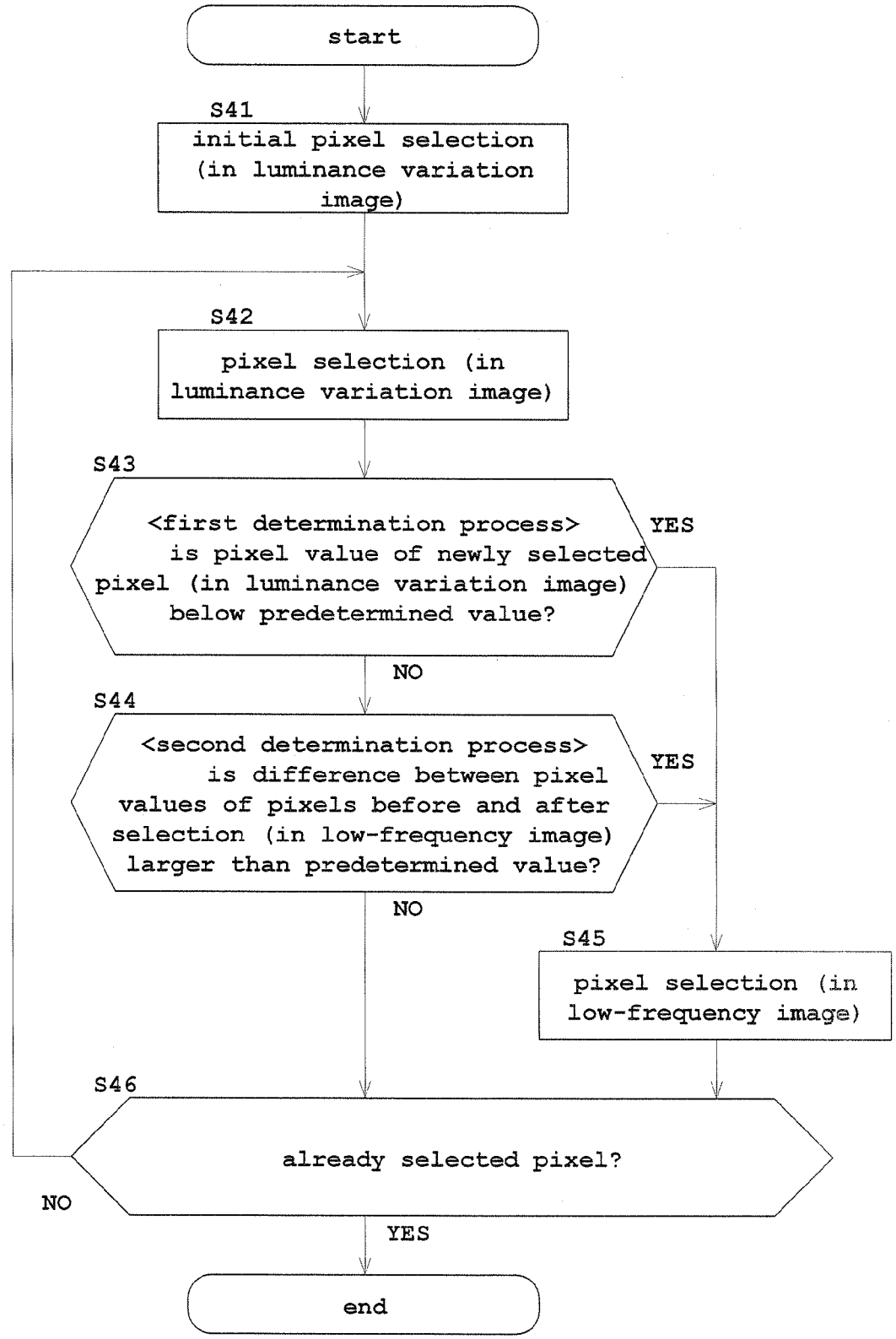
FIG. 8 is a flow chart showing operation of the boundary selecting unit.

Next, operation of the radiographic apparatus 1, and particularly operation of the image area extracting unit 11, will be described following the flow charts of FIGS. 7 and 8.

[Step S1] Image Pickup

Pushing an image pickup button not shown in FIG. 1 causes the radiation source 3 to emit radiation (e.g. X-rays), and the FPD 4 to start image pickup as interlocked therewith. The radiation emitted from the radiation source 3 passes through the patient M, and the FPD 4 detects the radiation transmitted through the patient M. The FPD 4 converts the detected radiation into electric signals corresponding to the intensity of the radiation, and outputs a radiological image. The radiological image outputted from the FPD 4 is converted into digital data by the analog-to-digital converter not shown, and is transferred to the image area extracting unit 11 of the image processor 5.

[Step S2] Generation of Low-Frequency Image

In the image area extracting unit 11, first, the radiological image picked up by the FPD 4 is once stored in the memory unit 13. The radiological image stored in the memory unit 13 is read therefrom, and is transferred to the low-frequency image generating unit 15. The low-frequency image generating unit 15 carries out a frequency filter process lower than the spatial frequency inside the area of patient M to generate a low-frequency image with reduced spatial resolution from the radiological image. The low-frequency image generating unit 15 generates a low-frequency image by reducing the inputted radiological image to generate a reduced image. The image reduction ratio of the radiological image, preferably, is about ⅛ to 1/10. Generating the low-frequency image provides stability since influences of noise components or fine structures (e.g. the ribs) inside the patient M are reduced. This facilitates recognition of a contour shape of the patient M, such as selection of boundary pixels located on the boundary of the area of interest, for example. The low-frequency image generated by the low-frequency image generating unit 15 is transferred to the luminance variation image generating unit 17 and boundary selecting unit 19.

[Step S3] Generation of Luminance Variation Image

The luminance variation image generating unit 17 generates a luminance variation image by calculating a luminance variation in each pixel based on the pixel value of each pixel in the low-frequency image generated by the low-frequency image generating unit 15. The luminance variations are derived from the luminance gradients of the image. The luminance gradients are derived from equation (1) to equation (3) noted hereinbefore.

[Step S4] Selection of Boundary Pixels

The boundary selecting unit 19 selects boundary pixels located on the boundary of the area of interest based on the pixel values of the low-frequency image generated by the low-frequency image generating unit 15 in step S2 and the luminance variation image generated by the luminance variation image generating unit 17 in step S3. The operation for selecting the boundary pixels by the boundary selecting unit 19 will be described with reference to the flow chart of FIG. 8.

[Step S41] Initial Pixel Selection (in Luminance Variation Image)

The boundary selecting unit 19 first selects a pixel with the largest variation, i.e. a pixel with the largest pixel value, from the luminance variation image (from an irradiation field range of the luminance variation image when the irradiation field is restricted by a collimator not shown in FIG. 1). Then, the boundary selecting unit 19 sets the selected pixel as an initial pixel (initial point) of pixels located on the boundary of the area.

[Step S42] Pixel Selection (in Luminance Variation Image)

Pixels adjacent and around the selected pixel are searched, and a pixel with the largest luminance variation is selected from among the adjacent pixels. When the selected pixel is the initial pixel, eight pixels adjacent the initial pixel and located in all directions therefrom are searched, and a pixel with the largest luminance variation is selected from among the eight pixels as a next boundary pixel. When the selected pixel is not an initial pixel, three adjacent pixels (pixel A, pixel B and pixel C) located in the direction of movement of pixel P(n) as shown in FIGS. 5A and 5B are searched, and a pixel having the largest luminance variation is selected from among the three pixels as a next boundary pixel.

[Step S43] First Determination Process

It is determined whether the pixel newly selected in step S42 is reliable as boundary pixel. That is, when the pixel value of the pixel newly selected in the luminance variation image is below a predetermined value, the newly selected pixel is determined low in reliability as boundary pixel (and the operation proceeds to step S45). When the pixel value of the pixel newly selected in the luminance variation image is larger than the predetermined value, the operation proceeds to step S44. The smaller luminance variation indicates the lower reliability as boundary pixel. Even if a pixel with a luminance variation below the predetermined value is selected in error, the pixel newly selected as boundary pixel is ruled out as low in reliability. This assures highly accurate and stable area extraction.

Step S44 Second Determination Process

A further determination is made on the newly selected pixel having undergone the determination process in step S43. Specifically, a comparison is made between pixel values of pixels in the low-frequency image corresponding in position to the newly selected pixel and a pixel before selection in the luminance variation image. When the difference is larger than a predetermined value, the newly selected pixel is determined low in reliability as boundary pixel (and the operation proceeds to step S45). When the difference is below the predetermined value, the operation proceeds to step S46. The pixel before selection refers to an immediately preceding pixel to be newly selected. The comparison is carried out to determine a difference between the pixel value of the newly selected pixel and the pixel value of the pixel before selection in the low-frequency image. The closer pixel values of adjacent pixels in the low-frequency image indicate the higher possibility of the pixels being in the same area. Even if the newly selected pixel is a pixel with a large luminance variation (i.e. even if the pixel value of the newly selected pixel and the pixel value of the pixel before selection are similar), pixel values can be widely different in the low-frequency image. In this case, the pixel newly selected as boundary pixel is ruled out as low in reliability, which assures highly accurate and stable area extraction.

In the determination processes in steps S43 and S44, the predetermined values are fixed values, without being limited thereto. That is, a value determined according to pixel values of the image may be set. For example, 10% of the pixel value range of the low-frequency image may be set as a predetermined value. Then, if the pixel value range of the low-frequency image is 120, the value set as the predetermined value will be 12 which is 10% of 120.

[Step S45] Pixel Selection (in Low-Frequency Image)

When the pixel is determined low in reliability in the determination processes of step S43 and step S44, boundary pixels are selected from the low-frequency image. Specifically, a pixel with the closest value to the pixel value of the pixel in the low-frequency image corresponding in position to the pixel before selection in the luminance variation image is selected from among pixels adjacent that pixel in the low-frequency image as a next boundary pixel. The closer pixel values of pixels in the low-frequency image indicate the higher possibility of the pixels being in the same area and being boundary pixels. Even when a pixel is determined low in reliability, the pixel selected can have high probability as boundary pixel. This assures highly accurate and stable area extraction. The boundary pixel selection is carried out by searching pixels located in all directions from a selected pixel, or three adjacent pixels located in the direction of its movement, as shown in step S42.

[Step S46] Determination as to Whether Already Selected Pixel or Not

It is determined whether the pixel newly selected in steps S42 and S45 has already been selected. If the pixel has not been selected, the operation returns to step S42 and repeats the same process. On the other hand, when the pixel has already been selected, the process of the boundary selecting unit 19 is ended. Reference is made to FIG. 7 again. Step S4 in FIG. 7 is completed and the operation proceeds to step S5. By repeatedly selecting boundary pixels as described above, the boundary pixels showing the outline of the area of interest of the patient M are selected. The selected pixels are outputted from the boundary selecting unit 19 as boundary pixel data.

[Step S5] Area Extraction Process

The area extraction processing unit 21 receives the boundary pixel data selected in step S4, the radiological image (original radiological image) stored in the memory unit 13 and before being converted into the low-frequency image, and the image reduction ratio used at the time of generating the low-frequency image. The area extraction processing unit 21 carries out a process of enlargement to the size of the original radiological image based on the boundary pixel data and image reduction ratio, and a process of extracting the area of interest from the original radiological image based on the enlarged boundary pixel data and original radiological image.

[Step S6] Adjustment Such as of Contrast

The radiological image with the area of interest of the patient M extracted by the image area extracting unit 11 is subjected to other required image processes such as adjustment of contrast in the area of interest by the image processor 5.

[Step S7] Image Display and Storage

The radiological image with the area of interest of the patient M extracted and having undergone the processes by the image processor 5 is displayed on the display unit 6 and stored in the memory unit 9.

According to the radiographic apparatus 1 described above, the low-frequency image generating unit 15 generates a low-frequency image from a radiological image by a frequency filter process lower than the spatial frequency in the area of patient M. The luminance variation image generating unit 17 detects luminance variations of the low-frequency image, and generates a luminance variation image. That is, influences of noise components or fine structural components inside the patient M are reduced by generating the low-frequency image, which facilitates recognition of a contour shape of the patient M. The luminance variation image generated from the low-frequency image provides the same effect as the low-frequency image. The boundary selecting unit 19 selects boundary pixels located on the boundary of the area of interest of the patient M based on the luminance variation image and low-frequency image. This assures highly accurate and stable area extraction.

The low-frequency image generating unit 15 generates a low-frequency image by reducing the size of a radiological image. This can generate a low-frequency image of lower frequency than with a usual filter, which realizes reduce influence of disturbance such as of noise, thereby assuring highly accurate and stable area extraction. Since the low-frequency image and luminance variation image have relatively small data amounts, the area of interest of the patient M can be extracted at high speed.

This invention is not limited to the foregoing embodiment, but may be modified as follows:

(1) In the foregoing embodiment, the boundary selecting unit 19 selects an initial pixel, and selects a next boundary pixel from pixels adjacent the selected pixel. The invention is not limited to this method. That is, boundary pixels located on the boundary of the area of interest may be selected based on pixels in the luminance variation image having larger pixel values than a predetermined value, and pixels detected by pixel values of pixels in the low-frequency image.

First, as shown in FIG. 9A, for example, a labeling process is carried out to detect, from the luminance variation image, pixels with larger luminance variations than a predetermined value. The pixels with larger luminance variations than the predetermined value are shown as pixels enclosed in thick lines. Next, as shown in FIG. 9B, a labeling process, for example, is carried out to select boundary pixels based on pixel values of the pixels in the low-frequency image, corresponding in position to the pixels with larger luminance variations than the predetermined value which are detected in the luminance variation image. When, for example, a lung field area is extracted, since the lung field area is lighter than surrounding areas, boundary pixels are selected by selecting pixels larger than a predetermined value from the low-frequency image. The selected boundary pixels are shown in FIG. 9C.

When the area of interest of the patient M to be extracted is darker than surrounding areas, in FIG. 9B, pixels of pixel values smaller the predetermined value are selected from the low-frequency image as boundary pixels. Alternatively, pixels of pixel values within a predetermined range may be selected from the low-frequency image as boundary pixels.

In FIG. 9A, for example, a labeling process may be carried out to detect, from the luminance variation image, pixels with larger luminance variations than a predetermined value, and in FIG. 9B, pixels larger than a predetermined value may be detected from the low-frequency image. Then, the pixels detected from both images may be made selected pixels.

(2) In the foregoing embodiment, the method of generating a low-frequency image by reducing a radiological image (reduction process by the low-frequency image generating unit 15), when reducing the radiological image to one eighth, for example, calculates an average of pixel values of 8×8 pixels, and generates a low-frequency image with the average value providing one pixel of a reduced image. The invention is not limited to this method. That is, a reduction method may be executed by thinning out pixels of the radiological image. When reducing the radiological image to one eighth, for example, a low-frequency image is generated by making an average pixel value of pixels remaining after 8×8 pixels are thinned out (e.g. 4×4 pixels indicated by sign T in FIG. 3A) one pixel. The thin-out can lessen amounts of data for calculation at the time of reduction process. It is possible to employ any other reduction methods commonly used.

(3) In the foregoing embodiment, the low-frequency image generating unit 15 generates a low-frequency image by reducing a radiological image. This invention is not limited to this method. Any other method commonly used for generating a low-frequency image may be employed. Such method includes, for example, a method of generating a low-frequency image by smoothing pixels by a filtering process which processes the pixels while shifting one pixel at a time, a method of generating a low-frequency image by converting a radiological image into a spatial frequency domain, cutting a high-frequency domain of the frequency domain converted, and converting a low-frequency domain into real space, or a combination of these methods.

The above method of generating a low-frequency image by converting a radiological image into a spatial frequency domain, cutting a high-frequency domain of the frequency domain converted, and converting a low-frequency domain into real space includes the following method. Specifically, a low-frequency image may be generated by converting a radiological image into a spatial frequency domain by Fourier transform, removing high-frequency components from the spatial frequency domain converted or passing only low-frequency components to obtain a low-frequency domain, and converting the low-frequency domain into real space by inverse Fourier transform. With this method using the Fourier transform and inverse Fourier transform, it is possible to generate a low-frequency image without changing image size. Instead of being limited to the Fourier transform, a process of wavelet conversion or Gabor filter may be carried out.

(4) In the foregoing embodiment, the luminance variation image generating unit 17 determines luminance gradients of the radiological image as luminance variations (amounts of characteristic) based on differences between pixel values in vertical and horizontal directions adjacent each pixel of a low-frequency image. The invention is not limited thereto. Any other known method may be used to determine luminance gradients. For calculation of luminance variations, a different process may be carried out as a method of extracting luminance variations of the image as characteristics, such as edge calculation by a 1D or 2D differential filter process such as of Sobel, Prewitt, Laplacian or Canny, or high-frequency component extraction by frequency processing.

Figure 10A:
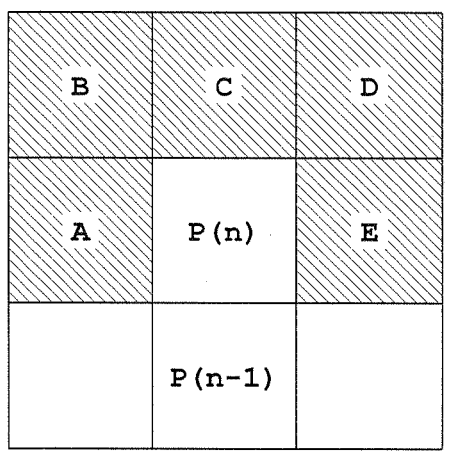
FIG. 10A is a view showing five pixels searched when a direction of movement is vertical or horizontal, in operation of a boundary selecting unit according to a modification.
Figure 10B:
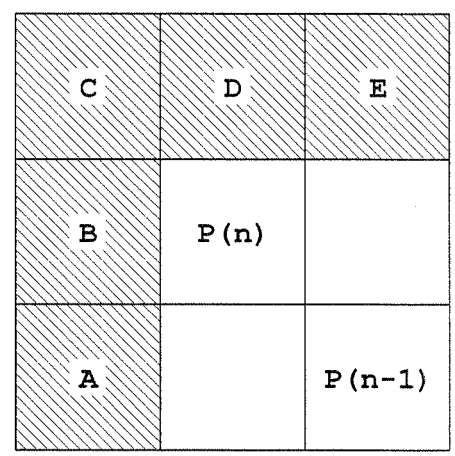
FIG. 10B is a view showing five pixels searched when a direction of movement is oblique, in operation of the boundary selecting unit according to the modification.

(5) In the foregoing embodiment, the boundary selecting unit 19 selects each boundary pixel by searching three adjacent pixels located in the direction of movement of a selected pixel. The invention is not limited thereto. As shown in FIGS. 10A and 10B, the boundary selecting unit 19 may select each boundary pixel by searching five adjacent pixels located in the direction of movement of a selected pixel.

(6) The foregoing embodiment has been described taking the lung field area of the chest as an example of an area of interest of the patient M to be extracted. This is not limitative. An area of interest of the patient M to be extracted may be other sites where image density and contrast differ greatly between inside and outside of the area of interest.

(7) In the foregoing embodiment, the radiographic apparatus 1 includes the flat panel radiation detector (FPD) 4 as radiation detector. This is not limitative. The radiographic apparatus 1 may have an image intensifier as radiation detector.

(8) The foregoing embodiment has been described taking X-rays as an example of radiation. This is not limitative. That is, the radiation may be gamma rays. For example, the radiation detector may detect gamma rays emitted from the patient M medicated with a radioisotope (RI).

(9) In the foregoing embodiment, the radiographic apparatus 1 simply includes the radiation source 3 and FPD 4. This is not limitative. It may be an X-ray CT apparatus for picking up sectional images with the radiation source 3 and FPD 4 rotating about the body axis of the patient M placed on the top board 2. Further, the apparatus may be constructed, as is a nondestructive testing apparatus for industrial use, which picks up images from objects carried on a belt conveyor.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiological image area extracting apparatus for extracting an area of interest of an object under examination from a radiological image picked up, the apparatus comprising:

a low-frequency image generating unit for generating a low-frequency image from the radiological image by a frequency filter process lower than a spatial frequency inside an object area;

a luminance variation image generating unit for generating a luminance variation image by detecting luminance variations of the low-frequency image; and a boundary selecting unit for selecting boundary pixels located on a boundary of the area of interest based on pixel values of the luminance variation image and the low-frequency image, and wherein the low-frequency image generating unit is arranged to generate the low-frequency image by reducing the radiological image.

2. The radiological image area extracting apparatus according to claim 1, wherein the radiological image is reduced, when a reduction ratio is 1/n, by making an average pixel value of n.times.n pixels a pixel value of one pixel.

3. The radiological image area extracting apparatus according to claim 2, further comprising an area extraction processing unit for carrying out a process for enlarging the boundary pixels selected by the boundary selecting unit to a size of the radiological image, and a process for extracting the area of interest from the radiological image.

4. The radiological image area extracting apparatus according to claim 2, wherein the boundary selecting unit is arranged to select the boundary pixels of the area of interest by selecting an initial pixel which is a pixel of maximum luminance variation from the luminance variation image, selecting as a next boundary pixel a pixel of maximum luminance variation from among pixels adjoining the selected initial pixel in all directions, and thereafter repeatedly selecting as a next boundary pixel a pixel of maximum luminance variation from among adjacent pixels located in a direction of movement of a selected pixel.

5. The radiological image area extracting apparatus according to claim 4, wherein the boundary selecting unit is arranged, when a pixel value of a pixel newly selected in the luminance variation image is below a predetermined value, to select as a next boundary pixel a pixel with a value closest to a pixel value of a pixel in the low-frequency image corresponding in position to a pixel before selection in the luminance variation image, from among pixels adjacent the pixel in the low-frequency image.

6. The radiological image area extracting apparatus according to claim 5, wherein the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image.

7. The radiological image area extracting apparatus according to claim 4, wherein the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image.

8. The radiological image area extracting apparatus according to claim 1, wherein the radiological image is reduced, when a reduction ratio is 1/n, by making an average pixel value of pixels thinned out of n.times.n pixels a pixel value of one pixel.

9. The radiological image area extracting apparatus according to claim 1, further comprising an area extraction processing unit for carrying out a process for enlarging the boundary pixels selected by the boundary selecting unit to a size of the radiological image, and a process for extracting the area of interest from the radiological image.

10. The radiological image area extracting apparatus according to claim 1, wherein the boundary selecting unit is arranged to select the boundary pixels of the area of interest by selecting an initial pixel which is a pixel of maximum luminance variation from the luminance variation image, selecting as a next boundary pixel a pixel of maximum luminance variation from among pixels adjoining the selected initial pixel in all directions, and thereafter repeatedly selecting as a next boundary pixel a pixel of maximum luminance variation from among adjacent pixels located in a direction of movement of a selected pixel.

11. The radiological image area extracting apparatus according to claim 10, wherein the boundary selecting unit is arranged, when a pixel value of a pixel newly selected in the luminance variation image is below a predetermined value, to select as a next boundary pixel a pixel with a value closest to a pixel value of a pixel in the low-frequency image corresponding in position to a pixel before selection in the luminance variation image, from among pixels adjacent the pixel in the low-frequency image.

12. The radiological image area extracting apparatus according to claim 11, wherein the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image.

13. The radiological image area extracting apparatus according to claim 10, wherein the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image.

14. The radiological image area extracting apparatus according to claim 1, wherein the boundary selecting unit is arranged to select the boundary pixels of the area of interest by selecting an initial pixel which is a pixel of maximum luminance variation from the luminance variation image, selecting as a next boundary pixel a pixel of maximum luminance variation from among pixels adjoining the selected initial pixel in all directions, and thereafter repeatedly selecting as a next boundary pixel a pixel of maximum luminance variation from among adjacent pixels located in a direction of movement of a selected pixel.

15. The radiological image area extracting apparatus according to claim 14, wherein the boundary selecting unit is arranged, when a pixel value of a pixel newly selected in the luminance variation image is below a predetermined value, to select as a next boundary pixel a pixel with a value closest to a pixel value of a pixel in the low-frequency image corresponding in position to a pixel before selection in the luminance variation image, from among pixels adjacent the pixel in the low-frequency image.

16. The radiological image area extracting apparatus according to claim 15, wherein the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image.

17. The radiological image area extracting apparatus according to claim 14, wherein the boundary selecting unit is arranged, when a result of comparison between pixel values of pixels in the low-frequency image corresponding in position to a newly selected pixel and a pixel before selection in the luminance variation image is larger than a predetermined value, to select as a next boundary pixel a pixel with a value closest to a pixel value of a pixel in the low-frequency image corresponding in position to the pixel before selection in the luminance variation image, from among pixels adjacent the pixel in the low-frequency image.

18. A radiological image area extraction program for causing a computer to carry out a process for extracting an area of interest of an object under examination from a radiological image picked up, the program being encoded in a computer readable medium and comprising:

a step of generating a low-frequency image from the radiological image by a frequency filter process lower than a spatial frequency inside an object area;

a step of generating a luminance variation image by detects luminance variations of the low-frequency image;

and a step of selecting boundary pixels located on a boundary of the area of interest based on pixel values of the luminance variation image and the low-frequency image, and wherein the low-frequency image generating unit is arranged to generate the low-frequency image by reducing the radiological image.

19. A radiographic apparatus for picking up images of an object under examination, the apparatus comprising:

a radiation detector for detecting radiation; and an image area extracting device for extracting an area of interest of the object from a radiological image outputted from the radiation detector; wherein the image area extracting device includes a low-frequency image generating unit for generating a low-frequency image from the radiological image by a frequency filter process lower than a spatial frequency inside an object area, a luminance variation image generating unit for generating a luminance variation image by detecting luminance variations of the low-frequency image, and a boundary selecting unit for selecting boundary pixels located on a boundary of the area of interest based on pixel values of the luminance variation image and the low-frequency image, and wherein the low-frequency image generating unit is arranged to generate the low-frequency image by reducing the radiological image.

* * * * *